(12) United States Patent
Kawaguchi et al.

(10) Patent No.: US 10,960,034 B2
(45) Date of Patent: Mar. 30, 2021

(54) MRSA INFECTION PROTECTIVE AGENT (71) Applicant: Nutri Co., Ltd., Mie (JP)

(72) Inventors: Susumu Kawaguchi, Mie (JP); Miho Kato, Mie (JP)

(73) Assignee: NUTRI CO., LTD., Mie (JP)

( * ) Notice: Subject to any disclaimer, the term of this patent is extended or adjusted under 35 U.S.C. 154(b) by 4 days.

(21) Appl. No.: 16/477,411

(22) PCT Filed: Jan. 25, 2018

(86) PCT No.: PCT/JP2018/002184
§ 371 (c)(1),
(2) Date: Jul. 11, 2019

(87) PCT Pub. No.: WO2018/139503
PCT Pub. Date: Aug. 2, 2018

(65) Prior Publication Data
US 2019/0374586 A1    Dec. 12, 2019

(30) Foreign Application Priority Data
Jan. 30, 2017   (JP) .............................. JP2017-013789
Jun. 13, 2017   (JP) .............................. JP2017-115577

(51) Int. Cl.
*A61K 35/741*   (2015.01)
*A61K 35/744*   (2015.01)
*A61P 31/04*    (2006.01)
*A61K 9/00*     (2006.01)

(52) U.S. Cl.
CPC .......... *A61K 35/744* (2013.01); *A61K 9/0053* (2013.01); *A61P 31/04* (2018.01)

(58) Field of Classification Search
CPC ................................................... A61K 35/741
See application file for complete search history.

(56) References Cited

FOREIGN PATENT DOCUMENTS

JP          8-283166         10/1996

OTHER PUBLICATIONS

Choi et al., "Heat-killed Enterococcus faecalis EF-2001 ameliorates atopic dermatitis in a murine model," Nutrients 8(146):1-11, Mar. 2016.*
Atya et al. ("Probiotic potential of Enterococcus faecalis strains isolated from meconium," Frontiers in Microbiology 6:1-9 (article 227), 2015.*
Extended European Search Report dated Sep. 21, 2020 in corresponding European Patent Application No. 18744179.5.
Database WPI AN 2003-869133 & JP 2003-261453, XP 2800247, 2003, 2 pages.

(Continued)

*Primary Examiner* — Rosanne Kosson
(74) *Attorney, Agent, or Firm* — Wenderoth, Lind & Ponack, L.L.P.

(57) ABSTRACT

Provided is a novel MRSA infection protective agent. Bacteria belonging to the genus *Enterococcus* have been found to be capable of protecting against MRSA infection. The MRSA infection protective agent comprises a bacterium belonging to the genus *Enterococcus*. Also provided are: a medicine for protection against MRSA infection, comprising a bacterium belonging to the genus *Enterococcus*; and a food for protection against MRSA infection, comprising a bacterium belonging to the genus *Enterococcus*.

11 Claims, 10 Drawing Sheets (56) References Cited

OTHER PUBLICATIONS

Database WPI AN 2017-79116Q & KR 2017 0123122, XP 2800248, 2017, 2 pages.
Choi et al., "Effect of *Enterococcus faecalis* EF-2001 on experimentally induced atopic eczema in mice," Food Science and Biotechnology, 2016, vol. 25, No. 4, pp. 1087-1093.
International Search Report dated Mar. 6, 2018 in International Application No. PCT/JP2018/002184.
Yoshida, Yuichi et al. 5. "Fundamental Discussion of Preventing Onset of MRSA Enterocolitis Using Probiotics Therapy", The Journal of the Japanese Society of Clinical Studies on Intestinal Microflora, 2015, vol. 7, No. 1, p. 21.
Chimura, Tetsuro. "Ecological Treatment of Bacterial vaginosis and vaginitis with Bio-Three". Japanese Journal of Antibiotics, 1998, vol. 51, No. 12, pp. 759-763, ISSN 0368-2781, table 1, etc.
Maitsubara, Yuiko, Ushijlma, Tsutomu. "Strong Antagonism of Probiotics against Entercococcus Faecalis and Clostridium butyricum against Methicillin-Resistant *Staphylococcus aureus*". Medicine and Biology, 1999, vol. 139, No. 4, pp. 185-190, ISSN 0019-1604, abstract, discussion, conclusion, etc.
Nohmi, Takao. "Prophylactic Effect of Enterococcus casseliflavus NF-1004 Preparation on the Lethal Infection of Mice with Opportunistic Pathogens". Jpn. J. Med. Mycol., 1996, vol. 37, pp. 175-179, ISSN 0916-4804, abstract, table 1, etc.
Yanagisawa, Takaharu et al. "*E. coli* Exclusion Promotion Effects using Lactic-Acid-Producing Bacterium Enterococcus faecalis EF-2001 Heat-Killed Bacterial Cells". Medicine and Biology, 2000, vol. 140, No. 3, pp. 53-56, ISSN 0019-1604, abstract, discussion, conclusion, etc.
Hara, Kosuke et al. "Efficacy of Heat-Killed Lactic Acid Bacteria Enterococcus faecalis on Methicillin-Resistant *Staphylococcus aureus* (MRSA) Infected Mice". J. New Rem. & Clin., 2018, vol. 67, No. 1, pp. 35-44, ISSN 0559-8672, abstract, discussion, conclusion, etc.
International Preliminary Report on Patentability dated Aug. 1, 2019 in International (PCT) Application No. PCT/JP2018/002184.
Yoshiki Obana et al., "The Virulence of Methicillin-Resistant *Staphylococcus aureus*", The Journal of the Japanese Association for Infectious Diseases, vol. 60, No. 10, pp. 1133-1139, 1986.

* cited by examiner

MRSA INFECTION PROTECTIVE AGENT

TECHNICAL FIELD

The present invention relates to an MRSA infection protective agent.

BACKGROUND ART

MRSA (methicillin-resistant *Staphylococcus aureus*) is a typical bacterium that causes healthcare-associated infection, and is a resistant bacterium that is the most frequently isolated in hospitals.

Anti-MRSA drugs approved in Japan include five drugs, namely vancomycin (VCM), teicoplanin (TEIC), arbekacin (ABK), linezolid (LZD), and daptomycin (DAP). Guidelines for treatment of MRSA infectious diseases have been formulated for proper use of the anti-MRSA drugs (Non Patent Literature 1).

In recent years, however, emergence of bacteria resistant to these anti-MRSA drugs has been reported, and there is a demand for development of a novel anti-MRSA drug.

CITATION LIST

Non Patent Literature

Non Patent Literature 1: Guidelines for Treatment of MRSA infectious Diseases, Jun. 9, 2013, Japanese Society of Chemotherapy

SUMMARY OF INVENTION

Technical Problem

An object of the present invention is to provide a novel MRSA infection protective agent.

Solution to Problem

As a result of intensive efforts, the present inventors have found that lactic acid bacteria belonging to the genus *Enterococcus* are capable of protecting against MRSA infection and have thus completed the present invention.

The gist of the present invention is as follows.

(1) An MRSA infection protective agent comprising a bacterium belonging to the genus *Enterococcus*.

(2) A medicine for protection against MRSA infection, comprising a bacterium belonging to the genus *Enterococcus*.

(3) A food for protection against MRSA infection, comprising a bacterium belonging to the genus *Enterococcus*.

(4) A method for prevention and/or treatment of MRSA infectious diseases, comprising administering a pharmaceutically effective amount of a bacterium belonging to the genus *Enterococcus* to a subject.

(5) Use of a bacterium belonging to the genus *Enterococcus* for prevention and/or treatment of MRSA infectious diseases.

(6) A bacterium belonging to the genus *Enterococcus* for use in a method for prevention and/or treatment of MRSA infectious diseases.

Advantageous Effects of Invention

The present invention enables protection against MRSA infection.

The present specification incorporates the contents of the specification and/or drawings of Japanese Patent Application Nos. 2017-13789 and 2017-115577 which are Japanese patent applications from which the present application claims priority.

DESCRIPTION OF EMBODIMENTS

Hereinafter, embodiments of the present invention will be described in more detail.

The present invention provides an MRSA infection protective agent comprising a bacterium belonging to the genus *Enterococcus*.

The bacterium belonging to the genus *Enterococcus* may be a lactococcus (e.g., *Enterococcus faecalis, Enterococcus faecium, Enterococcus avium, Enterococcus gallinarum,* or *Enterococcus casseliflavus*), and preferred is a lactococcus having biological response modifier (BRM) activity (YAKUGAKU ZASSHI, 112: 919-925, 1992; YAKUGAKU ZASSHI, 113: 396-399, 1992; Journal of Animal Clinical Research Foundation, 3: 11-20, 1994). *Enterococcus faecalis* is known as a lactococcus having BRM activity. *Enterococcus faecalis* EF-2001 strain is available from Nihon Berumu Co., Ltd. (2-14-3 Nagatacho, Chiyoda-ku, Tokyo).

*Enterococcus Faecalis*-2001 strain can be obtained from fecal matter of a normal person and has the following properties.

A Gram-positive coccus. Shape of colony (Trypto-Soya agar medium, 24-hour culture): 1.0-mm diameter, smooth, precise circle, white colony. Bacterial morphology: circular to oval (1.0×1.5 µm). Likely to form chains in liquid media. Non-spore-forming. Facultative anaerobic. Ferments glucose to produce lactic acid (final pH: 4.3). Non-gas-producing. Catalase-negative. Proliferates at 10 to 45° C. (the optimal temperature is 37° C.). Proliferates at pH 9.6 in 6.5% NaCl and 40% bile. Positive for 0.04% potassium tellurite. Positive for 0.01% tetrazolium. Positive for 0.1% methylene blue milk. Hydrolyzes arginine. Ferments amygdalin, cellobiose, fructose, galactose, glucose, glycerol, lactose, maltose, mannose, mannitol, ribose, salicin, sucrose, melicitose, and sorbitol to produce acids. Resistant at 60° C. for 30 minutes. Digests casein and gelatin. Decarboxylates tyrosine into tyramine. Lancefield antigen group; D. GC %: 35.0±1.0%.

The bacterium belonging to the genus *Enterococcus* may be a viable bacterium or a killed bacterium, and the cells may be subjected to a destruction treatment (e.g., homogenization, enzyme treatment, or ultrasonication) or any other treatment such as heating or drying (e.g., freeze-drying or spray-drying). The bacterium cells may be mixed with a diluent, and then a thickener may be added to form granules.

It is recommended to select the diluent and thickener from materials that are approved for addition to foods and medicines.

The MRSA infection protective agent of the present invention can be used for prevention and/or treatment of MRSA infectious diseases (MRSA infection). The MRSA infection protective agent of the present invention can be used as a medicine or a food additive.

The present invention provides a medicine for protection against MRSA infection, comprising a bacterium belonging to the genus *Enterococcus*.

When the MRSA infection protective agent is used as a medicine, the bacterium belonging to the genus *Enterococcus* may be used alone or be mixed with an excipient or a carrier to make a formulation such as a tablet, a capsule, a powder, a granule, a liquid, a syrup, an aerosol, a suppository, or an injection. The excipient or carrier may be any excipient or carrier that is commonly used in the art and is pharmaceutically acceptable, and the type and composition of the excipient or carrier can be chosen as appropriate. For example, water or a vegetable oil is used as a liquid carrier. As a solid carrier there can be used, for example, a sugar such as lactose, sucrose, or glucose, a starch such as potato starch or corn starch, or a cellulose derivative such as crystalline cellulose. A lubricant such as magnesium stearate, a binder such as gelatin or hydroxypropyl cellulose, and a disintegrant such as carboxymethyl cellulose may also be added. Further, an antioxidant, a colorant, a flavoring agent, a preservative, or the like may also be added. The medicine can also be used as a freeze-dried formulation.

The bacterium belonging to the genus *Enterococcus* can be administered by various routes, such as orally, nasally, rectally, transdermally, subcutaneously, intravenously, and intramuscularly.

The content of the bacterium belonging to the genus *Enterococcus* in the formulation varies depending on the type of the formulation, and is typically 0.001 to 100% by mass and preferably 0.01 to 100% by mass.

The dose of the bacterium belonging to the genus *Enterococcus* may be any pharmaceutically effective amount, i.e., any amount sufficient to exert the MRSA infection protective effect, and varies depending on the dosage form, the administration route, the age and body weight of the patient, the severity of the disease, and the like. In the case of an adult patient, for example, it is recommended to set the dose per administration to about $10^8$ to $10^{11}$ CFU/kg body weight, preferably about $6 \times 10^9$ to $1.2 \times 10^{10}$ CFU/kg body weight, in terms of the amount of the bacterium belonging to the genus *Enterococcus*, which may be given once to several times per day.

The bacterium belonging to the genus *Enterococcus* may be added to a food. The present invention provides a food for protection against MRSA infection, comprising a bacterium belonging to the genus *Enterococcus*.

The following may be added to the food of the present invention: general ingredients such as protein, fat, carbohydrate, and sodium; minerals such as potassium, calcium, magnesium, and phosphorus; trace elements such as iron, zinc, copper, selenium, and chromium; vitamins such as vitamin A, β-carotene, vitamin $B_1$, vitamin $B_2$, vitamin $B_6$, vitamin $B_{12}$, vitamin C, niacin, folic acid, vitamin $D_3$, vitamin E, biotin, and pantothenic acid; and other substances such as coenzyme Q10, α-lipoic acid, galacto-oligosaccharide, dietary fiber, an excipient (such as water, carboxymethyl cellulose, or lactose), a sweetener, a flavoring agent (such as malic acid, citric acid, or amino acid), and a fragrance. When the food of the present invention is provided as a liquid food, there can be used water, physiological saline, fruit juice, or the like as a liquid in which the food ingredients are to be dispersed or dissolved. In order to provide better taste in oral administration, it is recommended to use fruit juice.

The food of the present invention may be in any form such as a powder, a granule, a tablet, or a liquid. In order to ensure that sick or older persons cam easily take the food, the food is preferably a gelled product such as jelly.

Gelling agents that can be used include thickening polysaccharides such as dextrin, agar, xanthan gum, locust bean gum, carrageenan, and pectin, as well as gellan gum, psyllium seed gum, taxa gum, guar gum, glucomannan, alginic acid, tamarind seed gum, and cellulose; it is preferable to use one or two or more thickening polysaccharides. The gelled product preferably has, a gel strength at 5° C.' of 7,000±2,000 N/m², When the gel strength is 7,000±2,000 N/m², it is more preferable that the adhesion energy be 60±40 J/m³ and the cohesiveness be 0.7±0.1 J/m³, Gels having such low adhesiveness and high cohesiveness have excellent swallowability.

The gel strength can be measured as follows. Using a texturometer of YAMADEN Co., Ltd. and a 16-mm-diameter plunger as gel strength measurement instruments, measurement is carried out under the following conditions: the measurement temperature is 25° C., the compression, speed (the speed at which the plunger is pushed in) is 10 mm/s, the measurement strain (how much of the plunger is pushed in relative to the sample thickness) is 40.00%, the distance over which the plunger is pushed in is 10.00 mm, and the number of times the plunger is pushed in is two.

The adhesion energy can be measured as a negative energy required for pulling out the plunger after it is pushed in once in the above gel strength measurement.

The cohesiveness can be measured after the plunger is pushed in twice in the above gel strength measurement and calculated as the ratio between the energy for the first time it is pushed in and the energy for the second time it is pushed in.

The intake of the bacterium belonging to the genus *Enterococcus* may be any amount sufficient to exert the MRSA infection protective effect, and varies depending on the form of the formulation, the administration route, the age and body weight of the patient, the severity of the disease, and the like. In the case of an adult patient, for example, it is recommended to set the dose per administration to about $10^8$ to $10^{11}$ CFU/kg body weight, preferably about $6 \times 10^9$ to $1.2 \times 10^{10}$ CFU/kg body weight, in terms of the amount of the bacterium belonging to the genus *Enterococcus*, which may be given once, to several times per day.

EXAMPLES

Hereinafter, the present invention will be described in detail based on Examples. The present invention is not limited to these Examples.

Example 1

Figure 1:
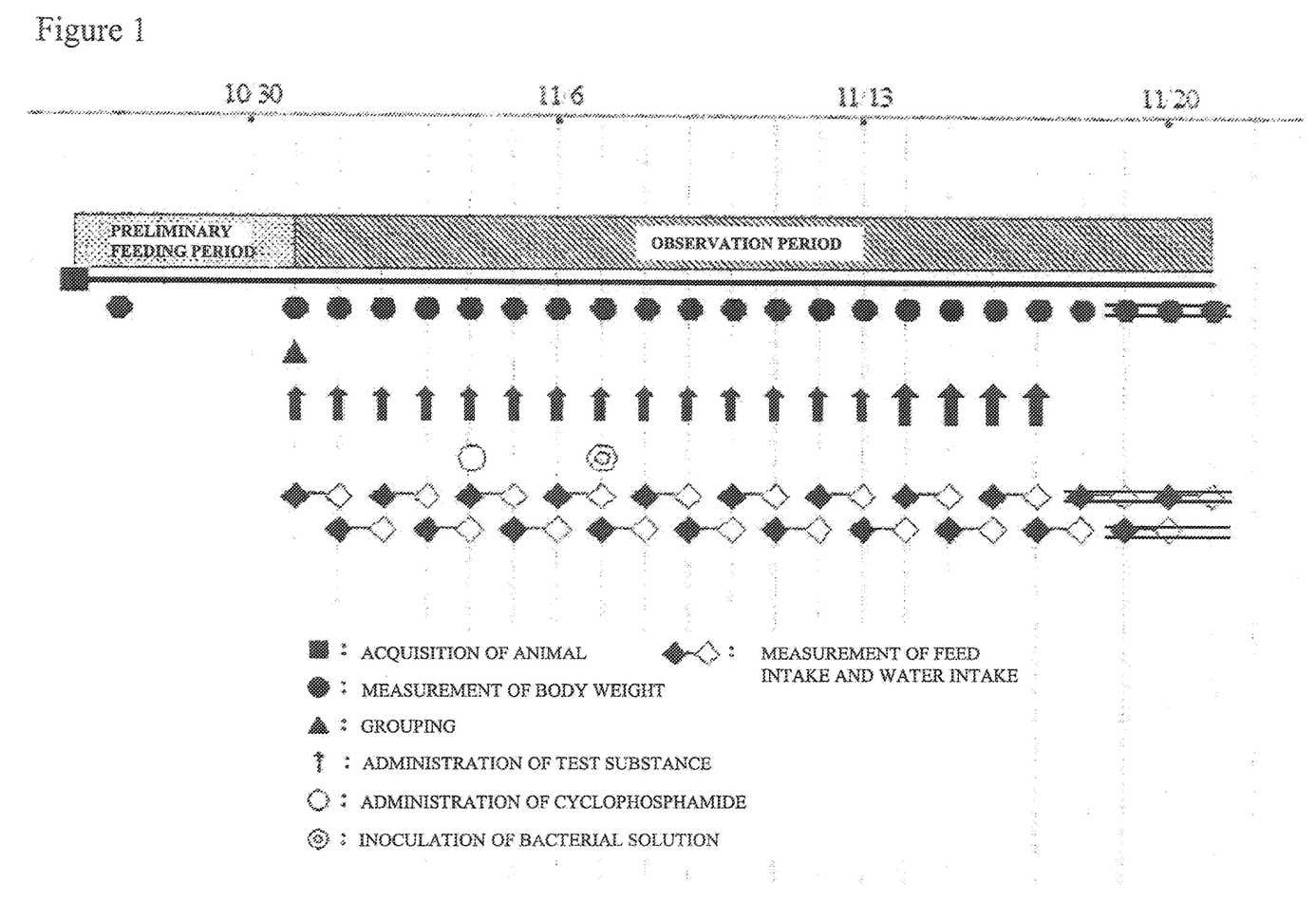
FIG. 1 shows a test schedule for Example 1.

Testing of Ability of Lactic Acid Bacteria EF-2001 Strain to Protect Against MRSA Infection Grouping: Comparison among three groups (n=10 for each group)
A: Control group
B: Lactic acid bacteria powder EF-2001 (40 mg/125 mL) group C: Lactic acid bacteria powder EF-2001 (80 mg/125 mL) group Testing method: Mice (BALB/C) at an age of four weeks were used, and a test substance (lactic acid bacteria powder EF-2001, Nihon Berumu Co., Ltd.) was orally administered once per day for one week. Thereafter, the mice were infected with methicillin-resistant *Staphylococcus aureus* (ATCC 43300, referred to as "MRSA" hereinafter); specifically, cyclophosphamide (100 mg of Endoxan (registered trademark) for injection, SHIONOGI & CO., LTD.) was intraperitoneally administered at a dose of 200 mg/kg (liquid volume: 10 mL/kg), and after three days 0.5 mL of an inoculum solution ($5 \times 10^6$ CFU) was intraperitoneally inoculated. The mice were observed for the subsequent two weeks (FIG. 1). For the control group, water for injection (Otsuka Pharmaceutical Factory, Inc.) was administered instead of the test substance. The feed (CRF-1, Oriental Yeast Co., Ltd.) and drinking water (tap water) were freely given.

Statistical method: The survival rate was calculated for each group. For the body weight, the average and standard deviation in each group were calculated. A Fisher's exact test was conducted as a significance test for the survival rate at the last day of observation between the control group and each of the treated groups. A Kaplan-Meier plot was drawn over the entire testing period, and a Logrank test was conducted. A p-value of 5% was considered significant, and separate indications were given for p-values of less than 5% and for p-values of less than 1%. For statistical analysis, a commercially available statistical program (SAS system, SAS Institute Japan) was used.

Examination items: Survival rate, body weight, feed intake, and water intake

Figure 2:
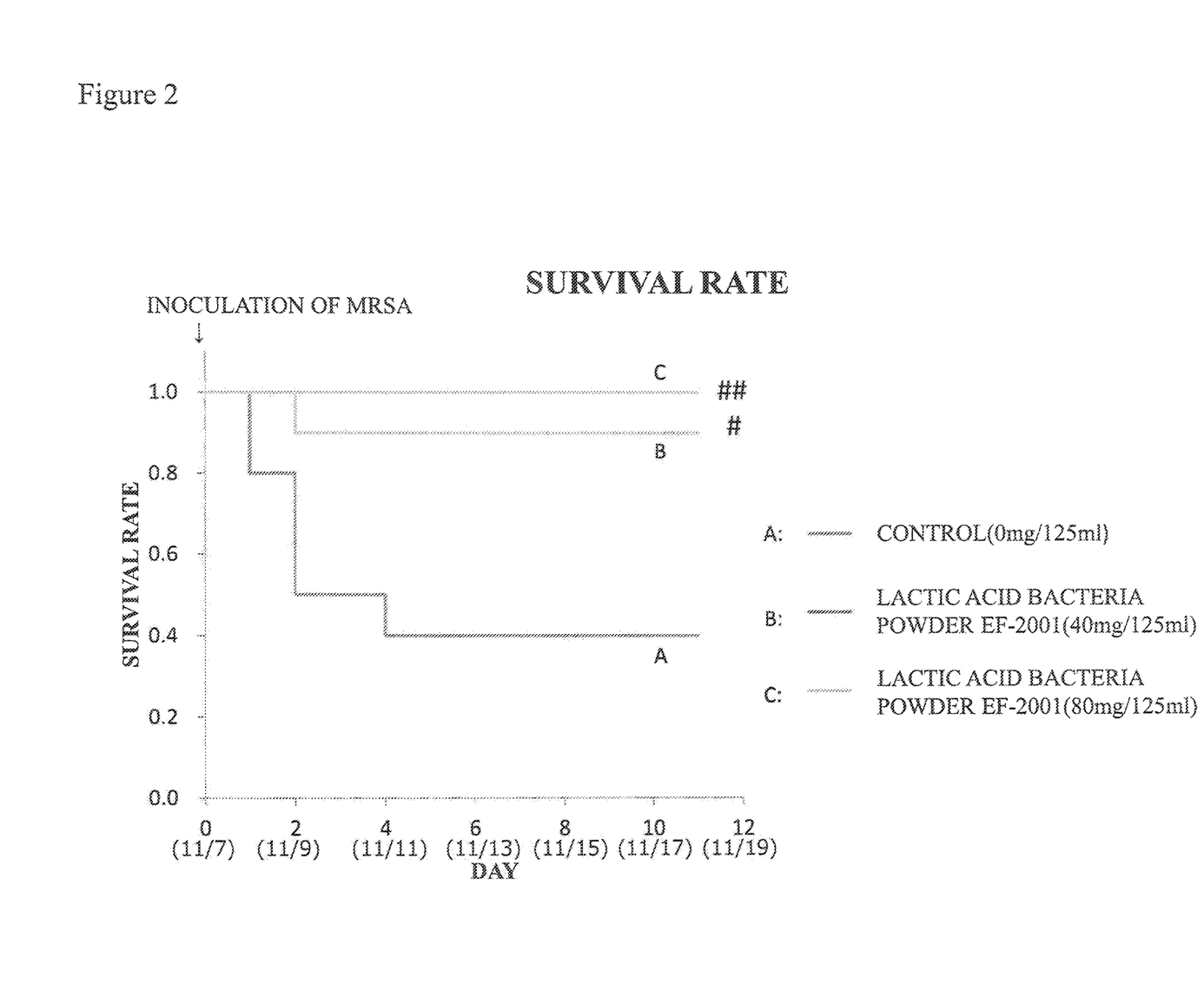
FIG. 2 shows a test result (survival rate) for Example 1.

Results:

Survival Rate (FIG. 2)

The survival rate of Group A was 40% at four days after inoculation of MRSA. Group A was compared with each of Groups B and C for the survival rate at 12 days after inoculation of MRSA and it was revealed that Groups B and C had significantly higher survival rates.

Figure 3:
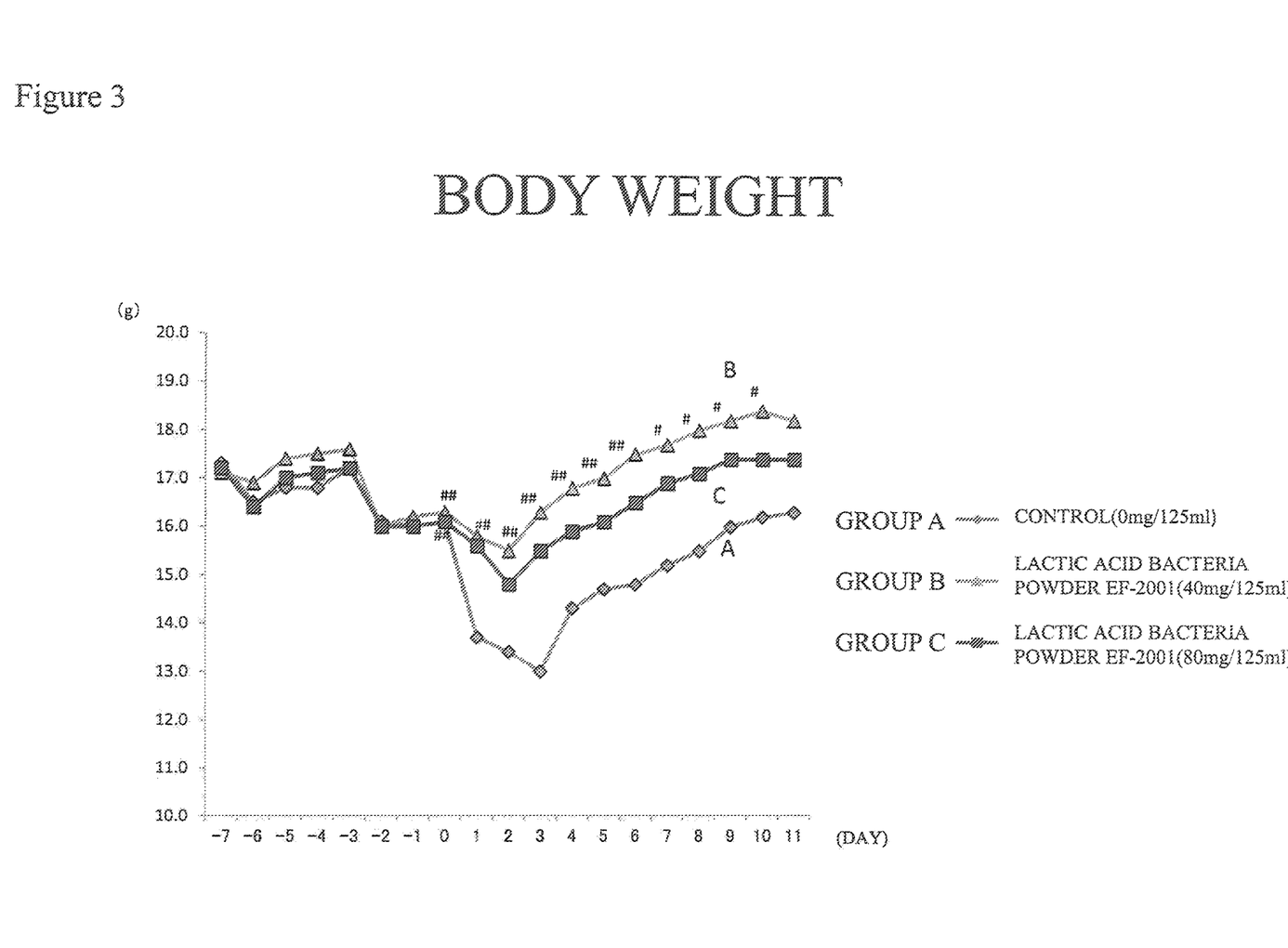
FIG. 3 shows a test result (body weight) for Example 1.

Body Weight (FIG. 3)

The body weight refers to the average body weight of surviving animals in each group. Group A had significantly lower values of body weight than Groups B and C at one day after inoculation of MRSA. In Group A, the body weight did not increase to the level before inoculation of MRSA even at 12 days of post-inoculation, while in Groups B and C, the body weight was restored to the level before inoculation of MRSA.

Figure 4:
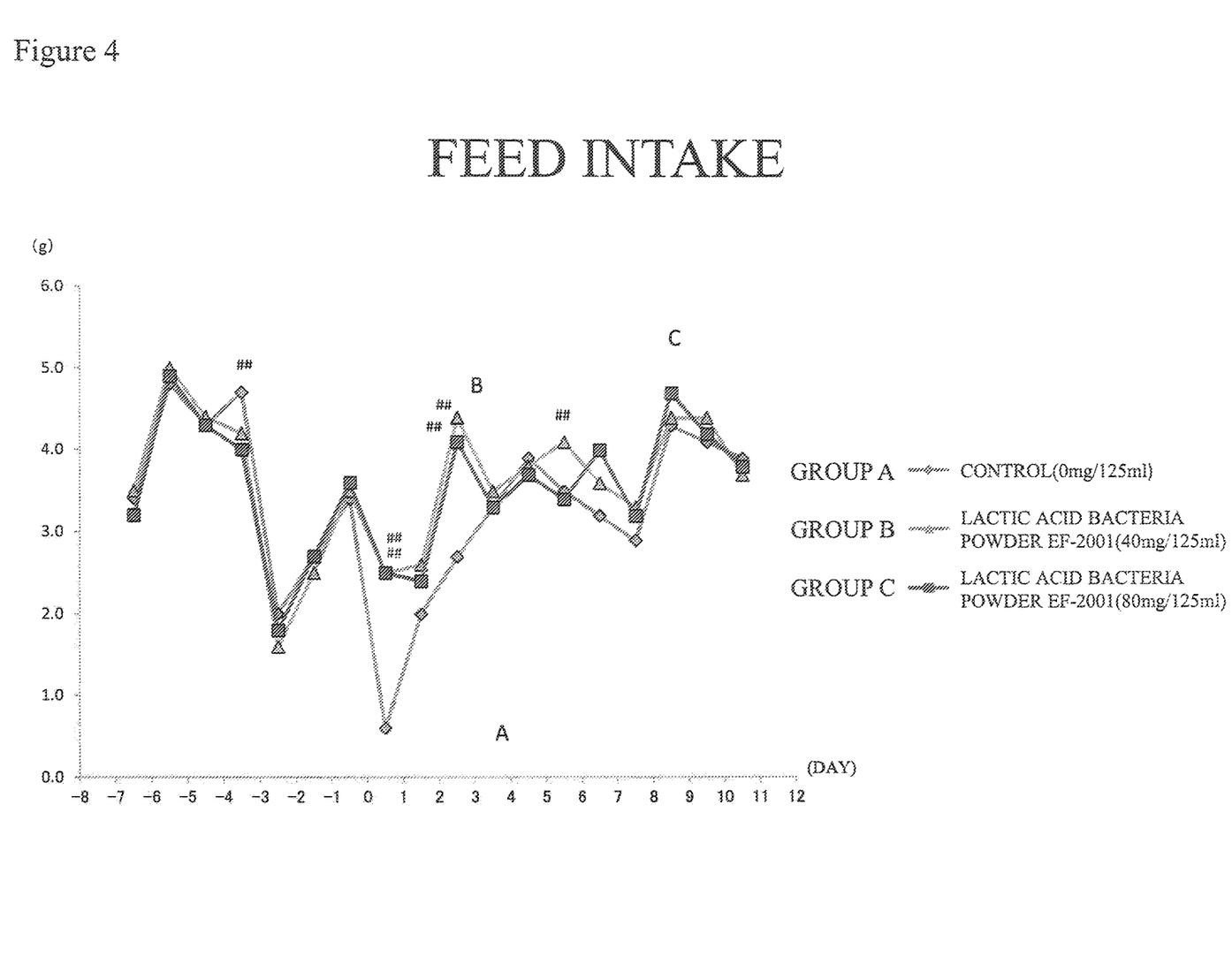
FIG. 4 shows a test result (feed intake) for Example 1.

Feed Intake (FIG. 4)

The feed intake of Group A was significantly lower than those of Groups B and C at one day after inoculation of MRSA.

Figure 5:
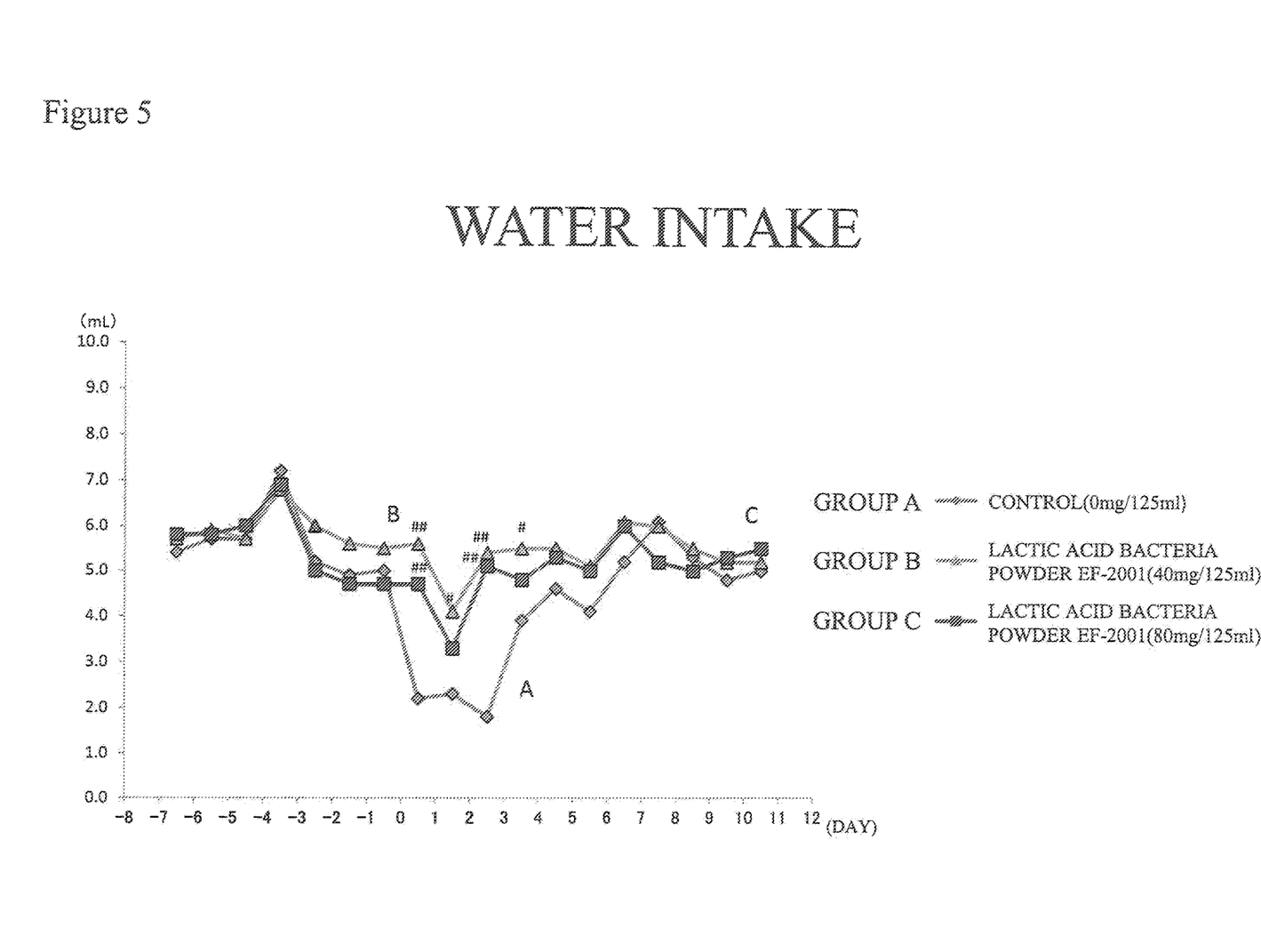
FIG. 5 shows a test result (water intake) for Example 1.

Water Intake (FIG. 5)

The water intake of Group A was significantly lower than those of Groups B and C at one day after inoculation of MRSA.

Example 2

Testing of Therapeutic Effect of Lactic Acid Bacteria EF-2001 Strain After MRSA Infection Grouping: Comparison between two groups (n=10 for each group)

A: Control group

B: Lactic acid bacteria, powder EF-2001 (80 mg/125 mL) group

Figure 6:
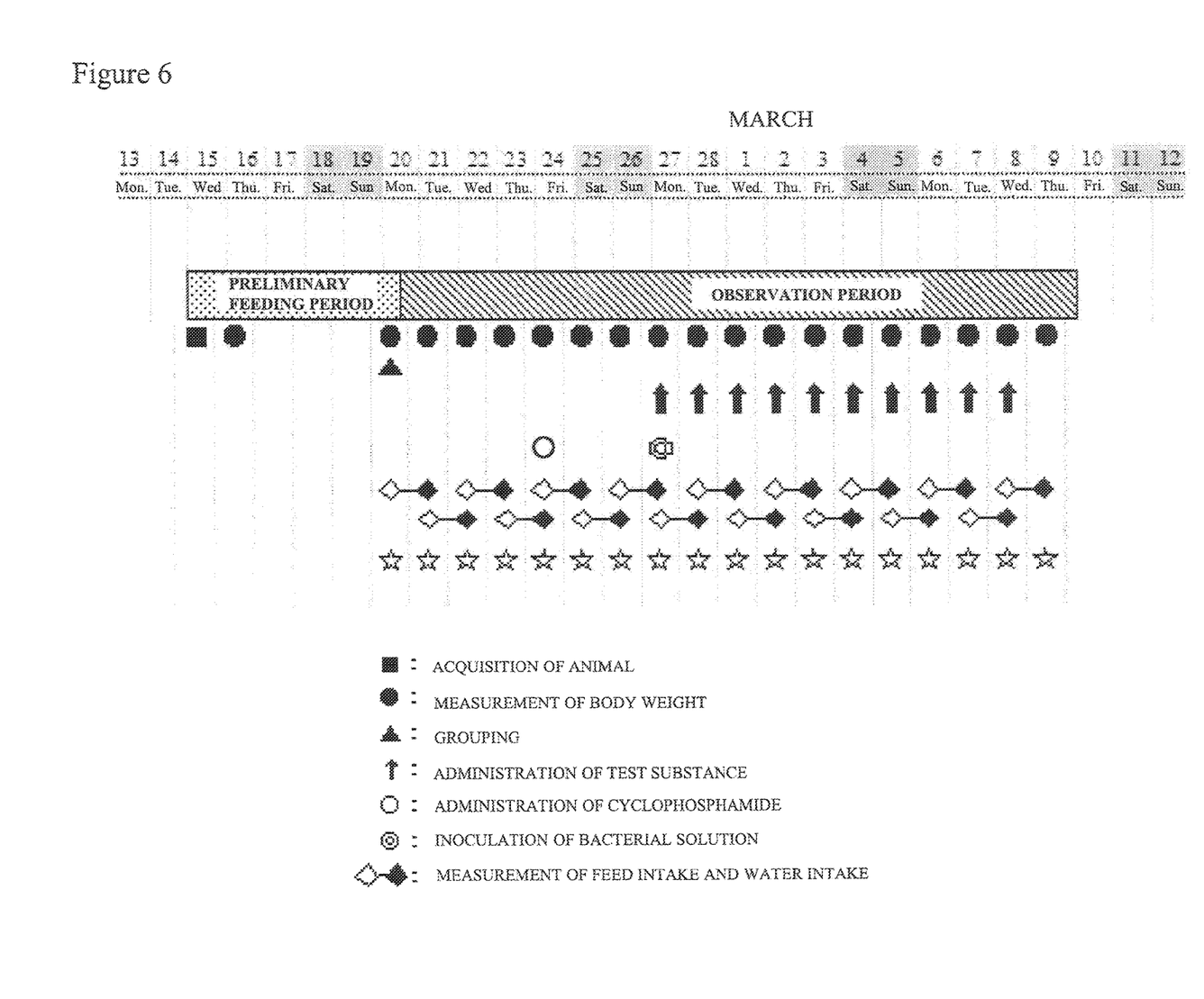
FIG. 6 shows a test schedule for Example 2.

Testing method: Mice (BALB/C) at an age of four weeks were used, and infected with methicillin-resistant *Staphylococcus aureus* (ATCC 43300, referred to as "MRSA" hereinafter); specifically, cyclophosphamide (100 mg of Endoxan (registered trademark) for injection, SHIONOGI & CO., LTD.) was intraperitoneally administered at a dose of 200 mg/kg (liquid volume: 10 mL/kg), and after three days 0.5 mL of an inoculum solution ($5 \times 10^6$ CFU) was intraperitoneally inoculated. After that, a test substance (lactic acid bacteria powder EF-2001, Nihon Berumu Co., Ltd.) was orally administered once per day for 10 days (FIG. 6). For the control group, water for injection (Otsuka Pharmaceutical Factory, Inc.) was administered instead of the test substance. The feed (CRF-1, Oriental Yeast Co., Ltd) and drinking water (tap water) were freely given.

Statistical method: The survival rate was calculated for both groups. For the body weight, the average and standard deviation in each of the two groups were calculated. A Fisher's exact test was conducted as a significance test for the survival rate at the last day of observation between the control group and the treated group. A Kaplan-Meier plot was drawn over the entire testing period, and a Logrank test was conducted. A p-value of 5% was considered significant, and separate indications were given for p-values of less than 5% and for p-values of less than 1%. For statistical analysis, a commercially available statistical program (SAS system, SAS Institute Japan) was used.

Examination items: Survival rate, body weight, feed intake, and water intake

Figure 7:
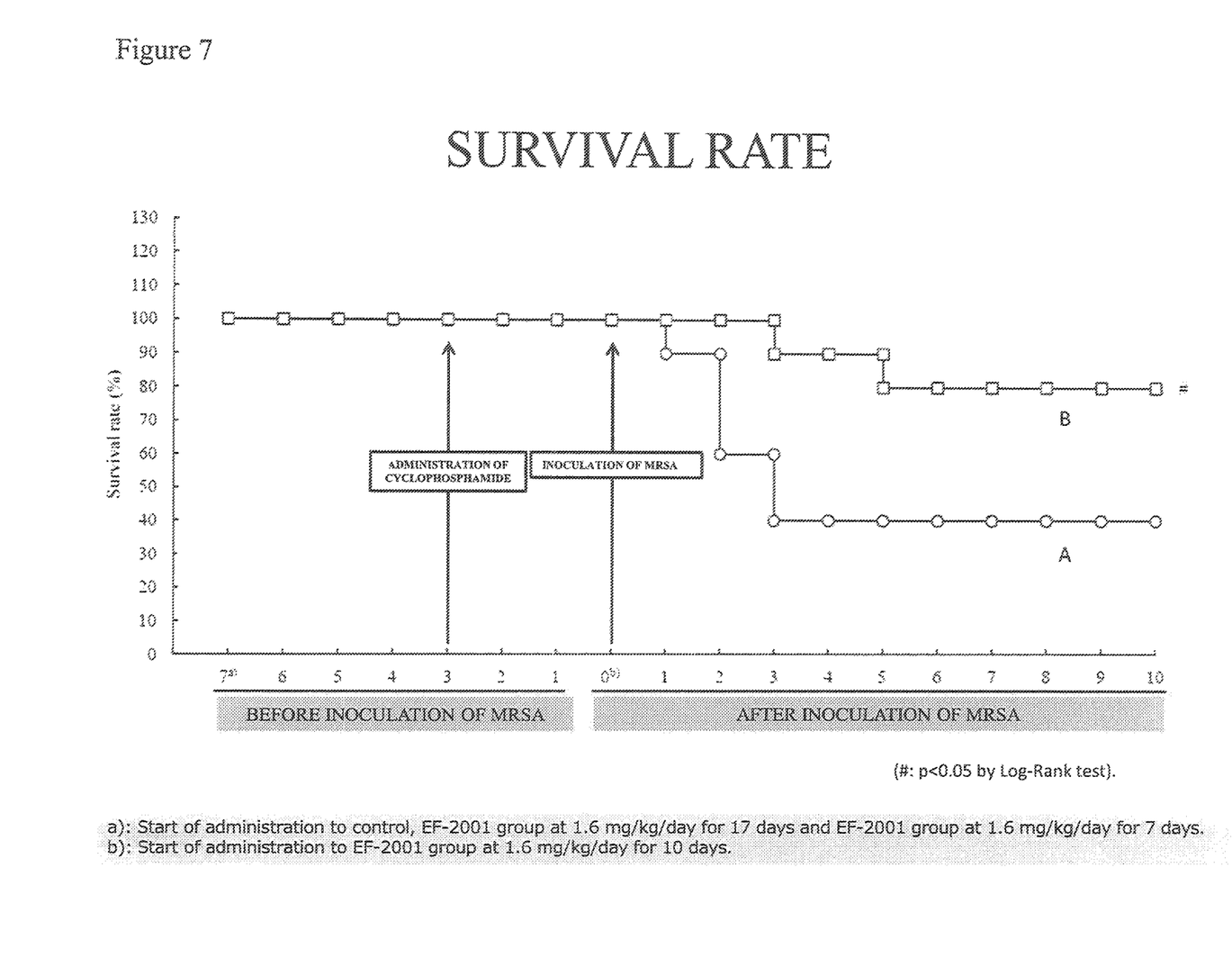
FIG. 7 shows a test result (survival rate) for Example 2.

Results:

Survival Rate (FIG. 7)

The survival rate of Group A was 40% at three days after inoculation of MRSA. Comparison between Groups A and B revealed that Group B had a significantly higher survival rate at 10 days after inoculation of MRSA.

Figure 8:
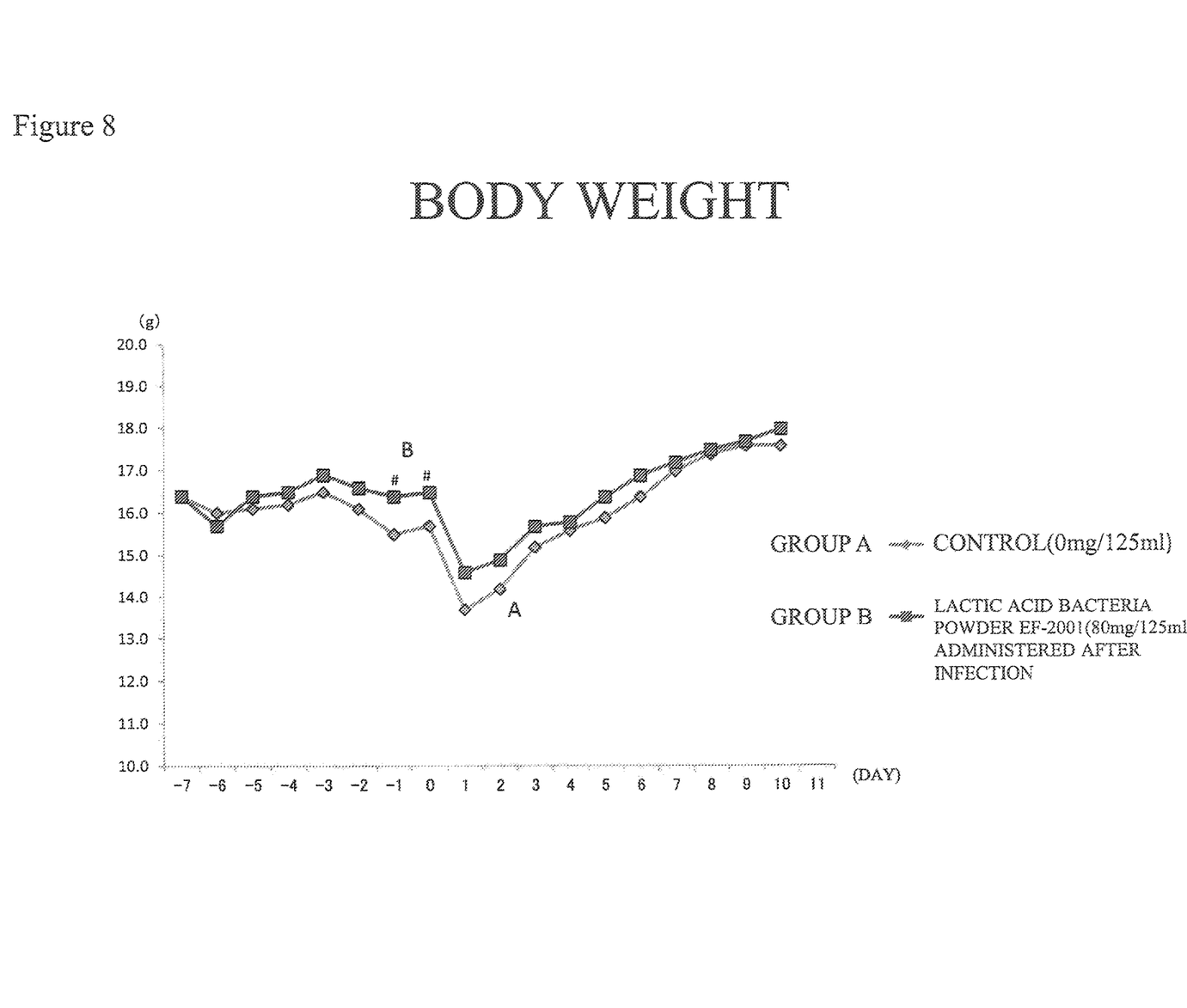
FIG. 8 shows a test result (body weight) for Example 2.

Body Weight (FIG. 8)

The body weight refers to the average body weight of surviving animals in each of the two groups. No difference in body weight was observed between the two groups after inoculation of MRSA, and the level before inoculation of MRSA was restored in both groups.

Figure 9:
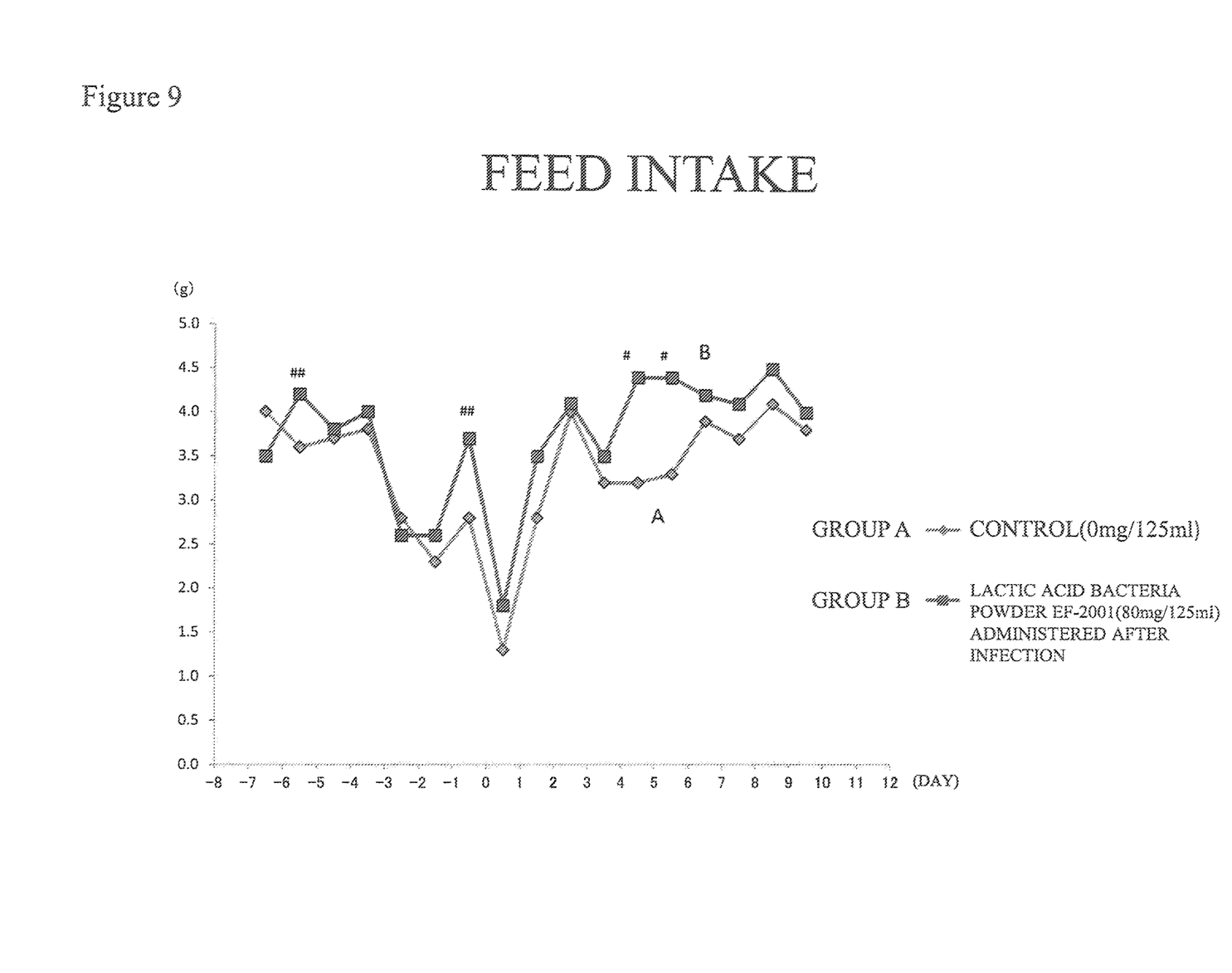
FIG. 9 shows a test result (feed intake) for Example 2.

Feed Intake (FIG. 9)

The feed intake of Group A was significantly lower than that of Group B at days 4 and 5 after inoculation of MRSA.

Figure 10:
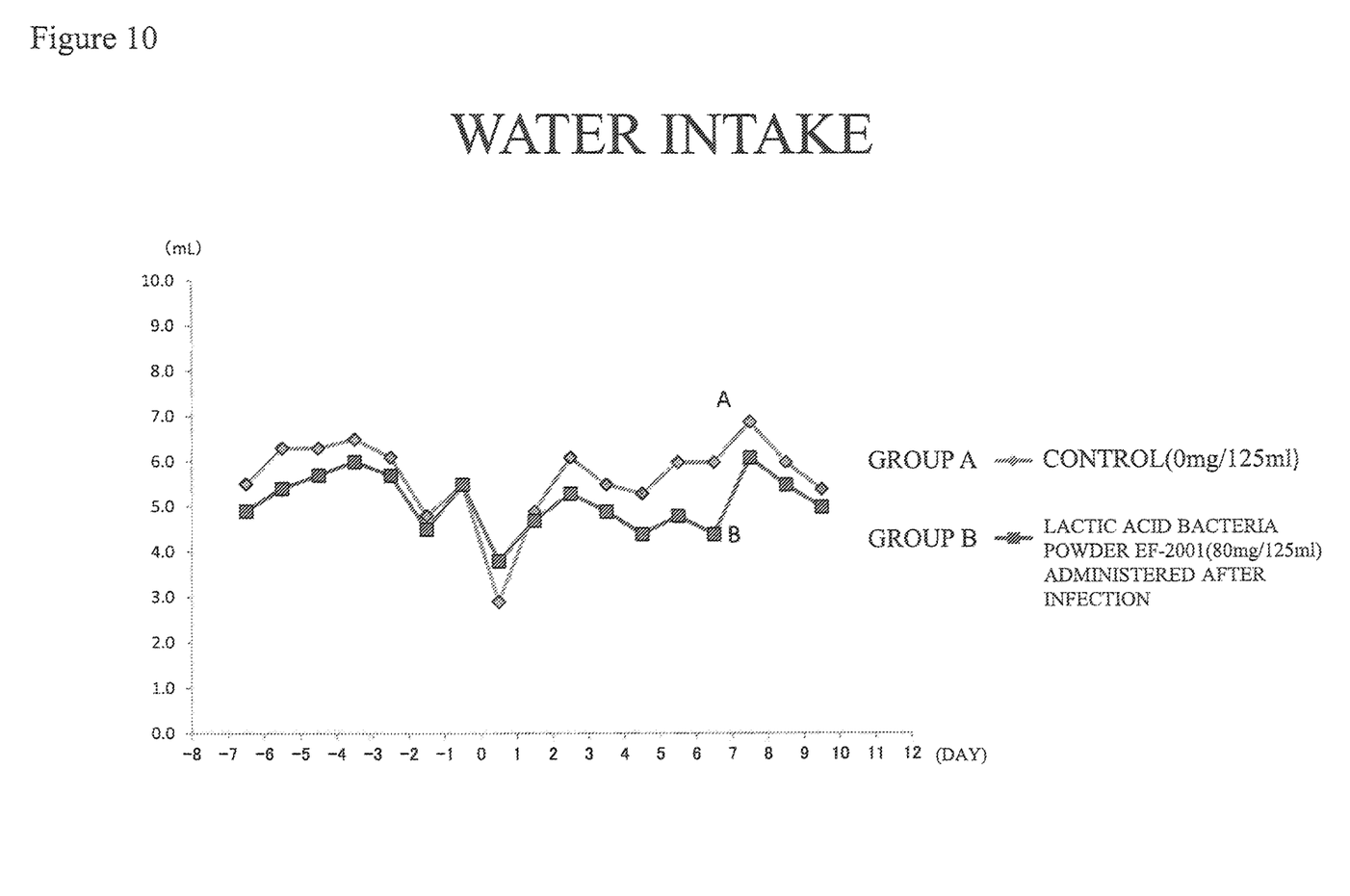
FIG. 10 shows a test result (water intake) for Example 2.

Water Intake (FIG. 10)

No significant difference in water intake was observed between the two groups.

The publications, patents, and patent applications mentioned herein are all incorporated herein by reference in their entirety.

INDUSTRIAL APPLICABILITY

The present invention is applicable to protection against MRSA infection.

The invention claimed is:

1. A method for reducing the incidence of and/or treatment of a methicillin-resistant *Staphylococcus aureus* (MRSA) infection in a subject in need thereof, comprising: administering to the subject a pharmaceutically effective amount of a composition comprising killed cells of *Enterococcus faecalis* strain EF-2001.

2. The method according to claim 1, wherein the method is a method for reducing incidence of the MRSA infection in the subject in need thereof.

3. The method of claim 2, wherein the composition is orally administered.

4. The method of claim 2, wherein the composition is formulated such that the killed cells of *Enterococcus faecalis* strain EF-2001 are orally administered in an amount of $6 \times 10^9$ CFU/kg body weight or more per dose.

5. The method of claim 2, wherein the composition is formulated such that the killed cells of *Enterococcus faecalis* strain EF-2001 are orally administered in an amount of $6 \times 10^{11}$ CFU/kg body weight or more per dose.

6. The method of claim 2, wherein the composition is formulated such that the killed cells of *Enterococcus faecalis* strain EF-2001 are orally administered in an amount of $6 \times 10^9$ to $1.2 \times 10^{10}$ CFU/kg body weight per dose.

7. The method according to claim 1, wherein the method is a method for treatment of the MRSA infection in the subject in need thereof.

8. The method of claim 7, wherein the composition is orally administered.

9. The method of claim 7, wherein the composition is formulated such that the killed cells of *Enterococcus faecalis* strain EF-2001 are orally administered in an amount of $6 \times 10^9$ CFU/kg body weight or more per dose.

10. The method of claim 7, wherein the composition is formulated such that the killed cells of *Enterococcus faecalis* strain EF-2001 are orally administered in an amount of $6 \times 10^{11}$ CFU/kg body weight or more per dose.

11. The method of claim 7, wherein the composition is formulated such that the killed cells of *Enterococcus faecalis* strain EF-2001 are orally administered in an amount of $6 \times 10^9$ to $1.2 \times 10^{10}$ CFU/kg body weight per dose.

\* \* \* \* \*